United States Patent

Jacobson

[11] Patent Number: 5,460,047
[45] Date of Patent: Oct. 24, 1995

[54] FLOW MEASUREMENT SYSTEM INCLUDING ULTRASONIC TRANSDUCERS

[75] Inventor: Saul A. Jacobson, Bellingham, Mass.

[73] Assignee: Panametrics, Inc., Waltham, Mass.

[21] Appl. No.: 396,070

[22] Filed: Feb. 28, 1995

Related U.S. Application Data

[63] Continuation of Ser. No. 975,855, Nov. 13, 1992, abandoned.

[51] Int. Cl.$^6$ .............................. G01N 29/00; G01F 1/20
[52] U.S. Cl. .................. 73/632; 73/861.18; 73/861.27; 73/597
[58] Field of Search ............................ 73/19.01, 19.03, 73/24.01, 24.06, 597, 598, 600, 599, 642, 861.18, 861.27, 861.28, 861.31, 632, 64.53, 64.49, 61.75, 861.29

[56] References Cited

U.S. PATENT DOCUMENTS

| | | | |
|---|---|---|---|
| 3,771,117 | 11/1973 | Shaffer et al. | 73/861.27 |
| 4,162,630 | 7/1979 | Johnson | 73/861.27 |
| 4,445,389 | 5/1984 | Potzick et al. | 73/861.27 |
| 4,555,951 | 12/1985 | Gutterman | 73/861.28 |
| 4,596,133 | 6/1986 | Smalling et al. | 73/24.01 |
| 4,838,127 | 6/1989 | Herremans et al. | 73/861.28 |

FOREIGN PATENT DOCUMENTS 162013  12/1981  Japan ..................... 73/861.28

OTHER PUBLICATIONS

Lawrence C. Lynnworth, *Ultrasonic Measurement for Process Control* Academic Press, Inc. 1989 pp. 306, 308, 357–358, 628–629.

*Primary Examiner*—Hezron E. Williams
*Assistant Examiner*—Nashmiya Ashraf

[57] ABSTRACT

A sensor system includes an ultrasonic transducer head with plural transducing elements. The elements are arranged in pairs with the first one of each pair lying in a first plane and the second one of each pair in a second plane spaced a half wavelength away. For transmission, the two are driven out of phase, while for reception their outputs are combined differentially. By changing the drive frequency the transmitted beam is steered to compensate for changes in transducer alignment, or changes in acoustic path caused by abnormal temperature, pressure or flow velocity. In another embodiment, an assembly has a plurality of transducers aligned along slightly divergent paths. Preferred systems employ an upstream and a downstream transducer assembly, each of which is used to alternately transmit and receive signal energy.

20 Claims, 5 Drawing Sheets

5,460,047

FLOW MEASUREMENT SYSTEM INCLUDING ULTRASONIC TRANSDUCERS

This application is a continuation of application Ser. No. 07/975,855 filed on Nov. 13, 1992, now abandoned.

BACKGROUND OF THE INVENTION

The present invention relates to apparatus for sensing fluid flow, and more particularly to sensing at high flow rates in a noisy environment, wherein the sensing is performed by transmitting and receiving ultrasonic signals along a path through the fluid. Such a high noise situation arises when a fast flowing fluid of low density is interrogated over a relatively long path, a situation encountered for example, when measuring the flow of stack gases. In the case of such flow, the level of noise arising in or carried by the surrounding wall, or the level of noise arising in the fluid itself, may each be large compared to the signal energy propagated and received through the fluid.

It often happens in a monitored process or condition, that the environment is hostile, inaccessible, or can be monitored only by sensors having a restricted range. All three of these limitations generally apply to stack measurements since the fluid may be at a temperature of several hundred degrees, must be interrogated by transducers mounted through the stack, often tens of meters above ground, and the transducers must be aimed at each other along a lengthy path which, although optimized for a particular expected fluid velocity, is subject to wandering as a fluid temperature, pressure and flow speed vary. When flow changes substantially, the interrogation beam becomes misaligned with the receiving transducer and signal quality drops.

By way of example, a typical stack gas sensing system may employ piezoelectric transducers mounted in vertically offset positions and aimed at each other from opposite sides of a three to ten meter diameter stack. Typically the transmitting and receiving transducers are of comparable size, and consist of a resonant electro-mechanical element mounted within a protective housing and coupled to a thin metallic diaphragm, about two to ten centimeters in diameter which directly transmits energy to the hot stack gases. The transducer assembly is mounted on a steel conduit that may extend into the stack, and may further include active fluid passages, for example, to carry a purge gas for preventing overheating of the transducer element.

Since the effective diaphragm area for coupling energy into or out of the rarified gas is small, and the path lengths are long, the level of the received signal of interest can be quite small compared to the level of noise generated elsewhere in the fluid, or reaching the transducer elements through the stack walls and transducer mounting structure. Moreover, the beam angle from the transmitting to the receiving transducer will generally change due to diffraction as the stack gas temperature varies, so even the gas-transmitted signal is subject to attenuation as the beam shifts.

Accordingly, it is desirable to enhance the overall signal quality in such systems.

BRIEF DESCRIPTION OF THE INVENTION

In accordance with a principal aspect of the present invention, a system for the ultrasonic interrogation of a flowing fluid to measure fluid characteristics employs a multi-transducer head, each transducer element of the head having a coupling face for coupling energy between that element and the flowing fluid, wherein each of several planes has one or more of the faces transmitting or receiving sonic energy. In accordance with a preferred aspect of the invention, a multi-transducer head is a receiving transducer that contains pairs of first and second transducer elements, the first element in each pair being offset by one-half wavelength from the second element of the pair, the wavelength being taken with respect to the intended fluid and sensing environment, e.g., temperature, pressure environment. A differential circuit combines the outputs. Since all elements are substantially identical in size, sensitivity, output characteristics and the like, this effectively doubles the level of the received signal while cancelling those components of the output signal resulting from noise carried though the conduit wall, transducer mounting, or housing.

According to another aspect of the invention, a transmitting transducer comprises one or more pairs of first and second transducers elements lying in first and second planes, respectively, the first and second planes being offset by one half wavelength. The first and second transducer elements are actuated with signals of opposite phase to produce an essentially plane wavefront. Most preferably, identical multi-transducer units are used for transmitting and for receiving, each being alternatively used for one purpose, then the other, so that one unit transmits while the other receives, and vice-versa, to develop upstream and downstream transit time measurements.

In accordance with yet another aspect of the invention, a presently preferred form of multi-transducer unit include a head piece having the form of a block into which a plurality of bores have been machined for receiving cylindrical-shaped transducer elements. The bores communicate with a central passage, which in turn is fitted to a hollow elongated member that serves both as a conduit for transducer electrode leads, and as a neck that extends, for example, from a conduit or stack wall, to position the transducer elements in or near the flowstream of the sensed fluid. A set screw, compression ferrule or gasket seals and secures the transducer element in each bore.

For implementing a system as discussed above, all bores are parallel, so only the depth of each transducer element must be set. However, in accordance with yet another embodiment of the invention, the bores holding transducer elements are not parallel, but each diverges by a small amount, e.g., 5°, from the central axis. The face of each element therefore lies in a plane that is skew with respect to the plane of each other element. With this arrangement, when all elements of a unit are actuated simultaneously they produce a broad-lobed composite beam. Thus, as flow conditions or the sensing environment change and the beam after propagating through the fluid, shifts off-center from the receiving transducer, the level of received power remains substantially constant.

BRIEF DESCRIPTION OF THE DRAWINGS

These and other features of the invention and its sundry embodiments will be best understood from the following figures, taken together with the following description, wherein.

DETAILED DESCRIPTION OF THE INVENTION

Figure 1:
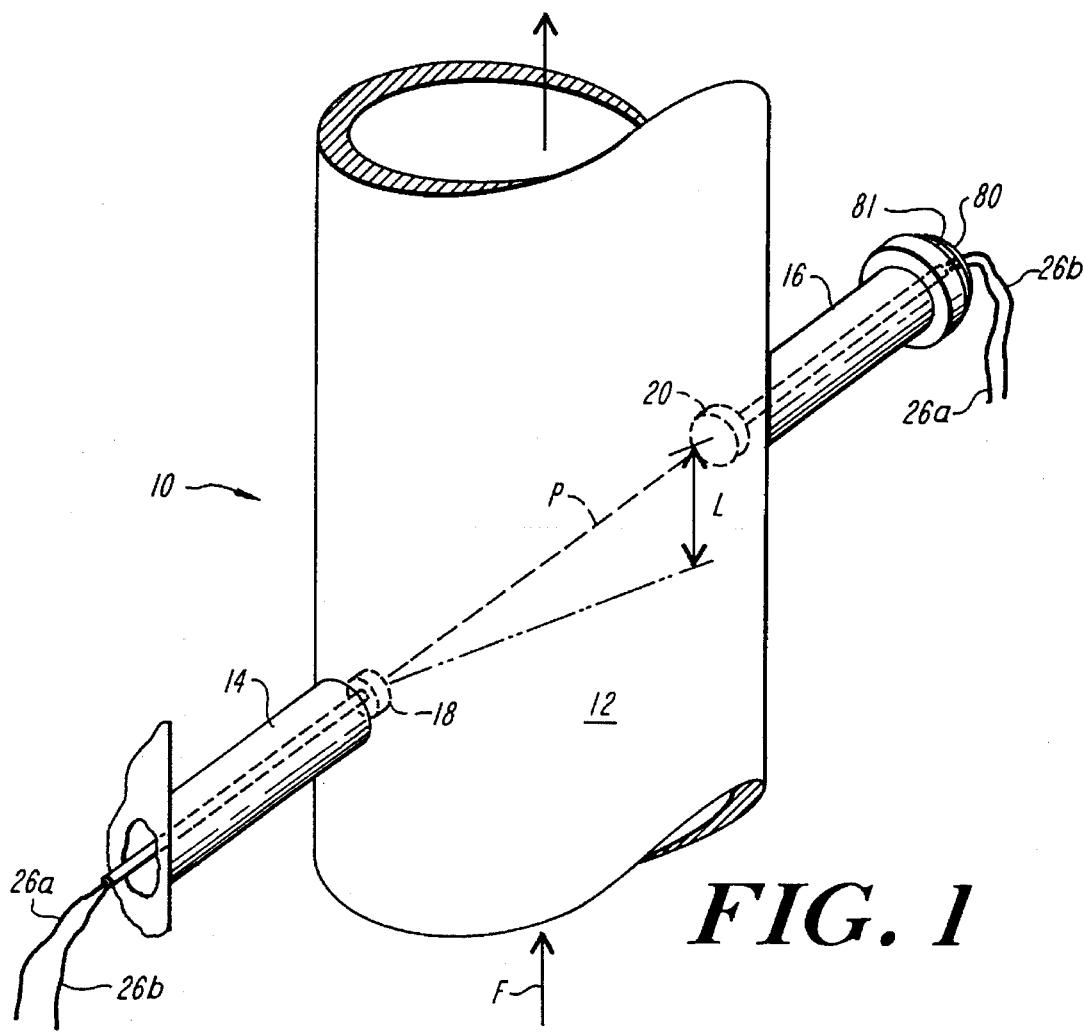
FIG. 1 is a general diagram of an ultrasonic flow measurement system.

FIG. 1 shows a flow sensing system 10 of the present invention, the layout and disposition of elements also being applicable to systems of the prior art employing conventional transducers. A fluid F flows in the general direction indicated by arrows, through a conduit 12 which confines and directs the flow. As discussed more fully below, the invention is advantageously applied to a variety of flow systems, but for uniformity of description the structure 12 will henceforth be referred to as a stack herein, it being understood therefore that the fluid F under discussion is a heated gas, or, more exactly, a mixture of gases. On opposite sides of stack 12 flanged access conduits 14, 16 are attached to the stack in positions offset by a length L along the direction of flow F, and positioned to define an interrogation path P between transducers. A transducer assembly 18 or 20 is mounted in each access conduit. Each transducer assembly has an elongated body or mounting structure, through which its electrical leads 26a, 26b are sheltered from the stack environment and brought out to processing or control circuitry (not shown).

The diagram of FIG. 1 is simplified, in that the active elements at the tip of the transducer assemblies 18, 20 may in fact be sheltered within the access conduits, slightly outside the stack wall, in which case the path P refracts as it enters and as it leaves the stack proper to the extent that temperature is not perfectly homogeneous along the entire acoustic path. In effect, the local temperature gradient acts like an acoustic wedge. The actual stack gas may vary in temperature or pressure across the conduit, leading to discrete or even continuous bending of the transit path. Further, the actual path followed by an interrogation signal is subject to drifting upstream or downstream as the flow velocity and environment change, so that the interrogation signal may be launched on a shallower or steeper path than P, and be carried upward or dragged downward to reach the opposing transducer. In this case, then, the receiving transducer will receive energy from the leading or trailing side of the transmission lobe, generally at a reduced energy level. Thus, the simple situation shown in FIG. 1 is modified in practice by diffraction and drift to achieve proper transducer location and orientation.

In the particular case of a stack the flowing medium is gaseous than thus has a sound propagation speed c on the order of several hundred meters per second, has a flow velocity up to around ten percent of that figure, and is subject to a great number of dynamically variable factors, such as cross currents, turbulence and standing resonances and compressional waves. The stack wall in which the transducers are mounted itself constitutes a rather noisy environment, and being generally formed of thick steel plate, it is subject to ringing and transmits all noise with little attenuation. However, in accordance with a principal aspect of the present invention, applicant takes advantage of the relatively high sound speed c in the stack wall by providing a multi-element receiving transducer that removes this extraneous noise.

The transducer assembly is mounted on a flange 80 via a shaft or pipe (shown in phantom in FIG. 1) that supports the transducer head. A gasket 81 is fitted between flange 80 and a corresponding flange on the stack nozzle 14 or 16. Advantageously, in accordance with one aspect of the present invention, gasket 81 is formed of a highly attenuating material, such as Teflon, and has a thickness when installed and heated to its operating temperature, of one-quarter wavelength of the transducer signal frequency in that material. For a 50 kHz transducer, this is approximately one quarter inch. This isolates the transducers from noise and crosstalk.

Figure 2:
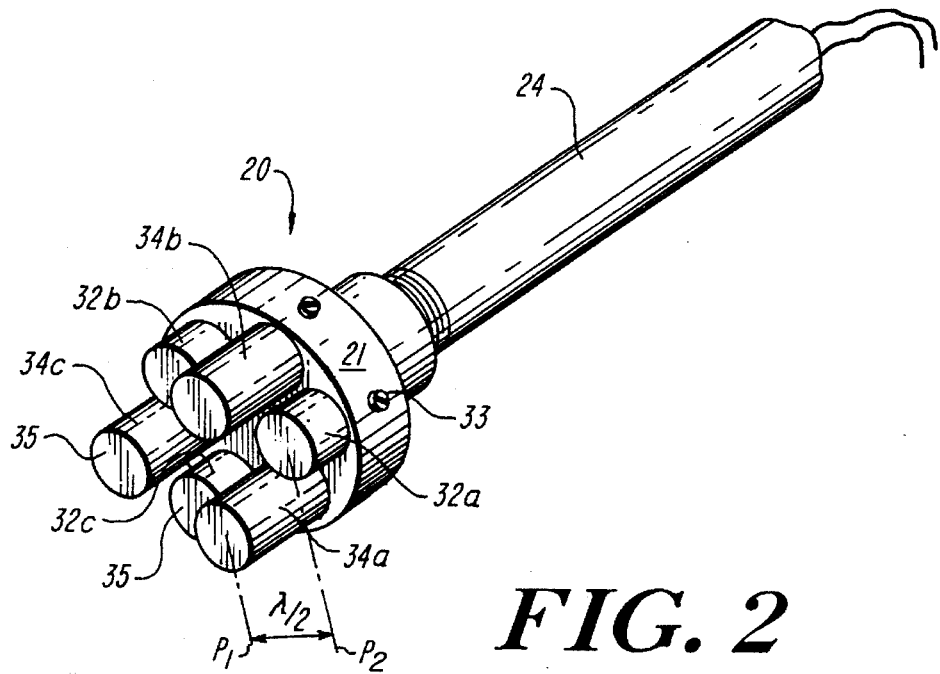
FIG. 2 is a perspective view of transducer unit in accordance with a presently preferred form of the invention.

As shown in FIG. 2, a receiving transducer assembly 20 according to this aspect of the invention includes a body having a head 21 in which a plurality of transducer elements 32a–32c and 34a–34c are mounted. A positioning arm or shaft 24, extends from the head 21 and generally defines the transmission axis. Head 21 has a plurality of bores for receiving the transducer elements, each element being secured at a selected depth by a set screw 33. The transducer elements may be conventional transducers, mounted in cylindrical shells or tubes, such as the Panametrics model no. T1 or T2 flare gas transducers, sold by Panametrics, Inc. of Waltham Mass. and used, for example, with their Model 7100 or subsequent line of ultrasonic interrogation units.

The transducer assembly of FIG. 2 has a first set of transducer elements 34a–34c mounted such that their front faces 35 lie in a first common plane P1, and a second set of transducer elements 32a–32c mounted so that their faces 35 lie in a second common plane P2, the first and second common planes being separated by $\lambda/2$ where $\lambda$ is a wavelength of the transducer signal in the medium which is to be measured. By way of example, for use in a combustion gas, predominantly air at 300° F. using 50 kHz resonant transducer elements, a transducer face offset of about 0.156 inches is used.

Figure 2B:
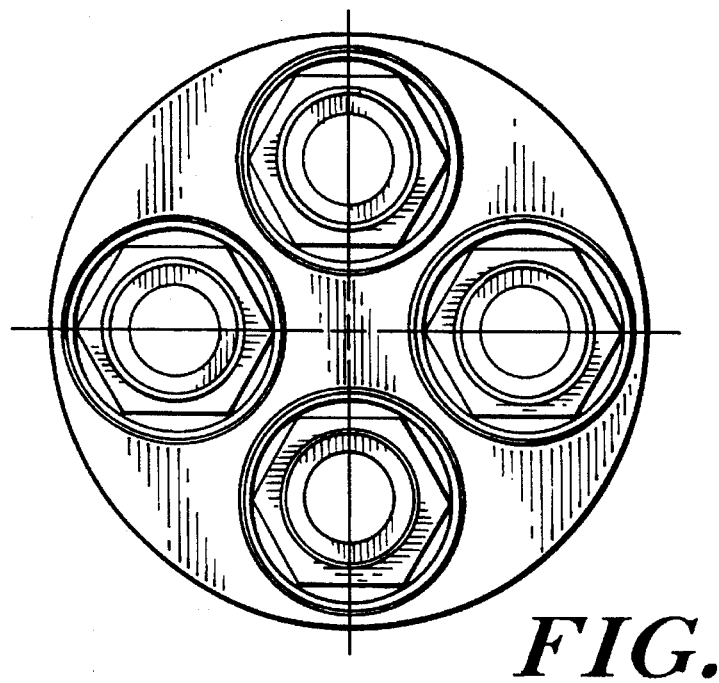
FIGS. 2A and 2B are face and sectional views of another embodiment of the invention.
Figure 2A:
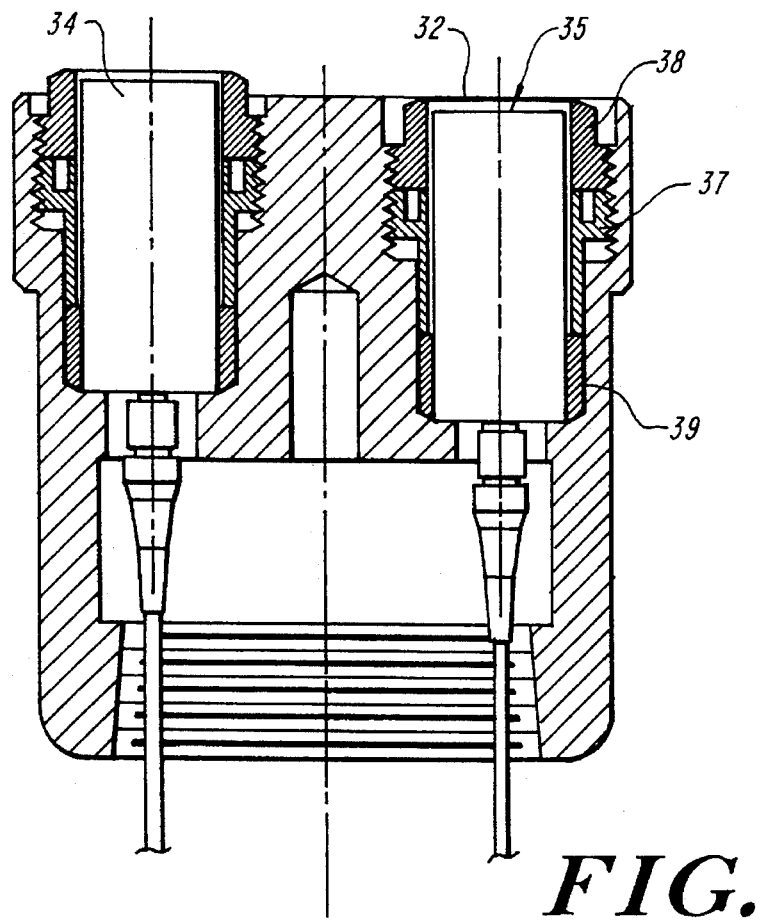

FIGS. 2A and 2B show face and sectional views of the head portion 21 and transducer mounting of another embodiment, similar to that of FIG. 2 but having four transducer elements. As shown, the out-of-phase transducers 34, 32 are fitted into threaded bores and secured by locking threaded members, namely, a long nut 37, and a short nut 38 which are adjustable to set the height of the transducer face 35. A TEFLON packing sleeve 39 seals the transducer seat.

Figure 3:
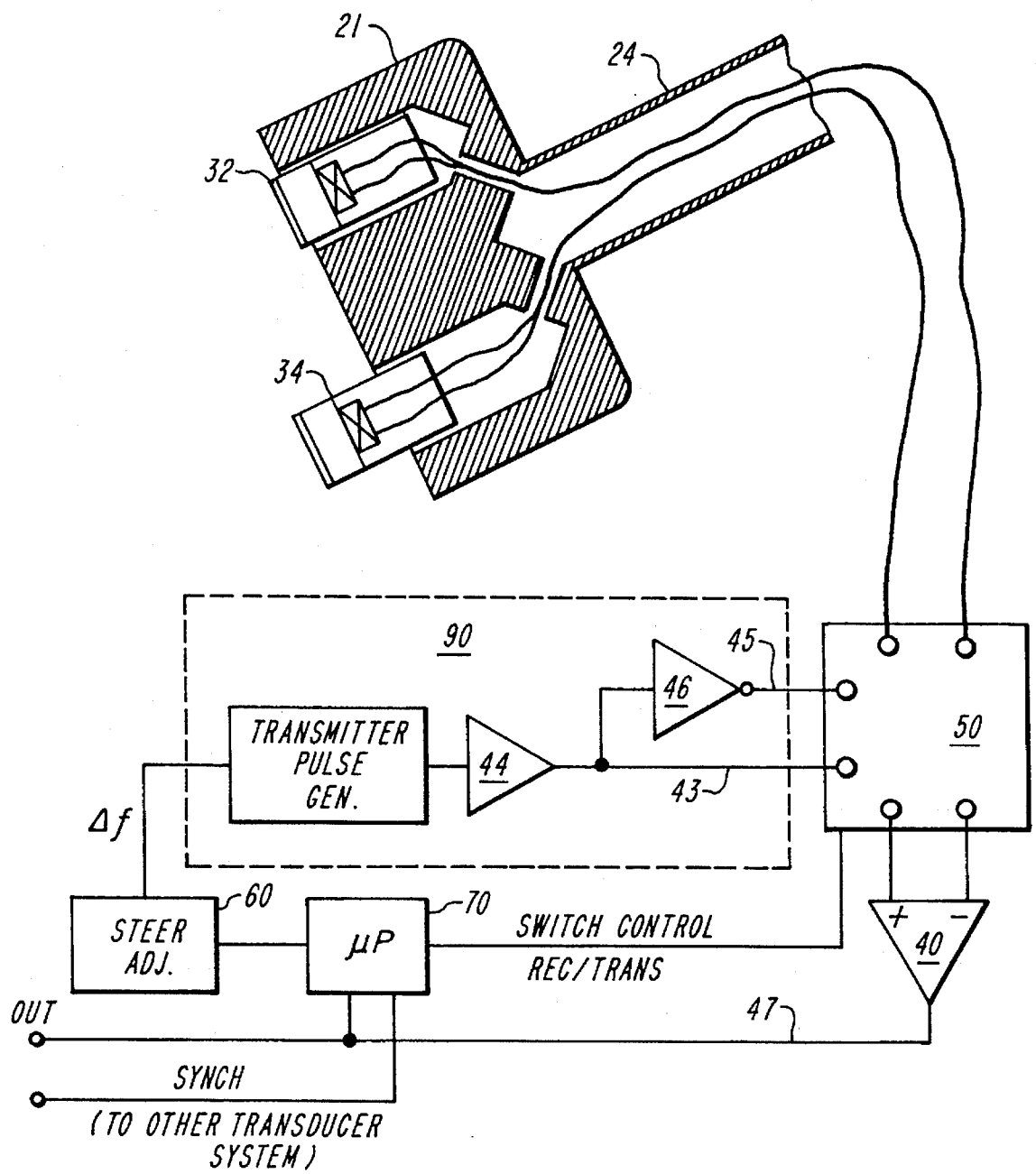
FIG. 3 shows signal transmission and reception with the preferred embodiment.

FIG. 3 shows the reception and transmission circuit configuration used for the arrangement of offset transducer elements of FIG. 2. Each element 32 in one plane is paired with another element 34 in the other plane, and the outputs of the pair are fed to a differential amplifier 40 that combines them 180° out of phase. The elements 32, 34 are, except for position, identical, with substantially matching output characteristics. Moreover, being firmly anchored in the head 21, elements of a pair both receive noise propagated through the solid steel body of shaft 24 and head 21. Since these elements have a soundspeed on the order of three to six thousand m/sec, the noise from this source reaches both transducers 32, 34 substantially simultaneously and is independent of the degree of offset of the transducer faces 35. Accordingly, conduit/mounting noise is essentially cancelled out, while the magnitude of the out-of-phase signals received through the fluid is augmented, essentially doubled by the differential combination.

It has been assumed in the foregoing discussion that a 50 kHz signal having a substantially flat wavefront has been transmitted across the fluid as an interrogation signal. The transmitted signal may be generated by a conventional transducer, but preferably, the transmitting transducer assembly 18 (FIG. 1) also has a multi-element transducer head, essentially identical in construction to the receiving assembly 20.

FIG. 3 shows the actuation circuitry 90 for utilizing assembly 20 as a transmitter. An ultrasonic pulse train, e.g., a 50 kHz square wave signal, is provided along line 41 to amplifier 44 which puts out a transducer drive signal on line 43. This drive signal is coupled directly to one transducer 34, while an out-of-phase replica is placed on line 45 via inverter 46. By driving the offset element out of phase, an in-phase wave is produced. Thus, the offset pairs of transducer elements 32, 34 are driven to produce a broad flat wavefront.

The use of a multiple element phase-inverted array for transmission in this manner is expected to produce a large, well directed powerful beam.

Furthermore, as the flow velocity or temperature changes, the beam may be expected to wander from the path P. According to another aspect of the invention, the beam is steered back into alignment by providing to the transmission pulse generator a frequency variation signal $\Delta f$ to select a higher or lower frequency of transmission pulses. Frequency modifier 60 may be controlled by a microprocessor 70 which evaluates the strength of the received signal on line 47 and initiates a sequence of programmed changes to cause frequency selector 60 to sequentially modify the frequency of transmission to a higher or lower frequency until a detected quality of reception indicates that path alignment has been achieved. As the frequency is varied, the wavelength changes, and any bending of the beam which may have occurred due, for example, to increased stack temperature and changing sound speed gradients, especially near the wall or cavity into which the transducer radiates, is corrected, bringing the transmitting path back into alignment with the receiving transducer.

In accordance with yet another aspect of the invention, a transducer assembly includes a body having plural transducer elements mounted therein, each element being tilted slightly to produce a beam that diverges from the central axis of the assembly by a small angular offset, e.g., five degrees.

Figure 4:
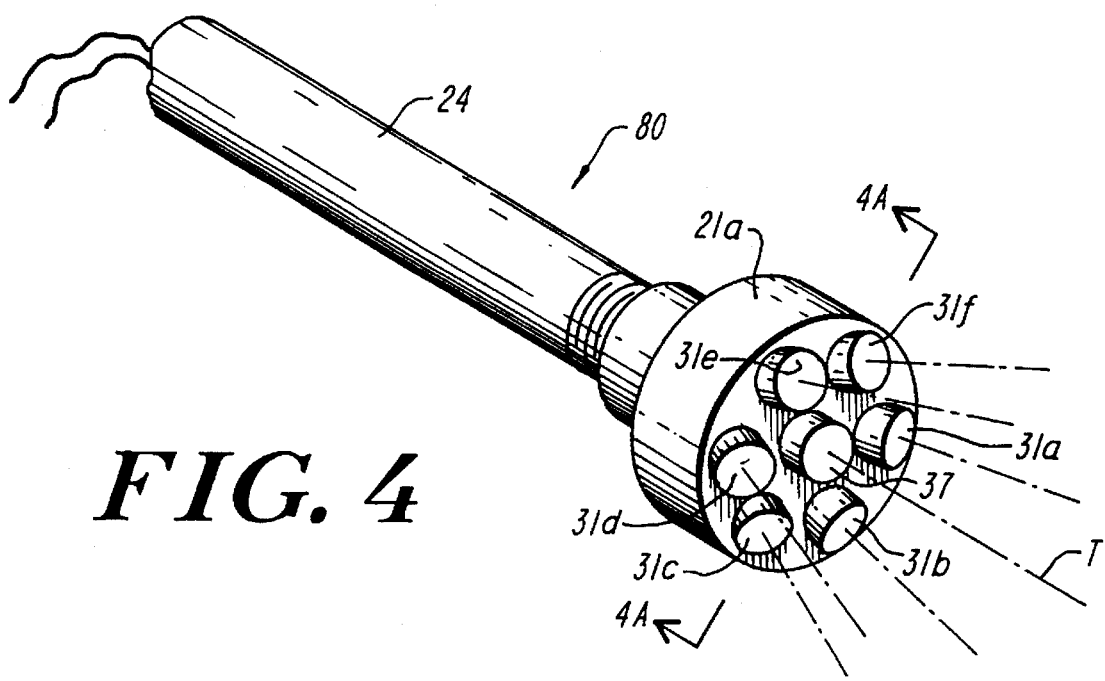
FIG. 4 shows a perspective view of another embodiment of a transducer unit.

FIG. 4 shows a transducer assembly 80 in accordance with this aspect of the invention. As before, the assembly preferably contains a mounting shaft 24 and head 21a, the head in this instance having a plurality of equispaced bores or openings (not numbered) arranged around the periphery of its front face. Each bore holds one transducer element of which six, 31a through 31f, are shown by way of illustration. Preferably, there are an even number of such elements, e.g., between two and ten such elements, all being equispaced (e.g., n elements located at the vertices of a regular n-gon) and each being inclined outwardly a small amount (e.g., two to ten degrees) from the central axis "T" of the assembly. As before, the elements may be conventional elements such as the above identified Panametrics stack gas transducers.

Figure 4A:
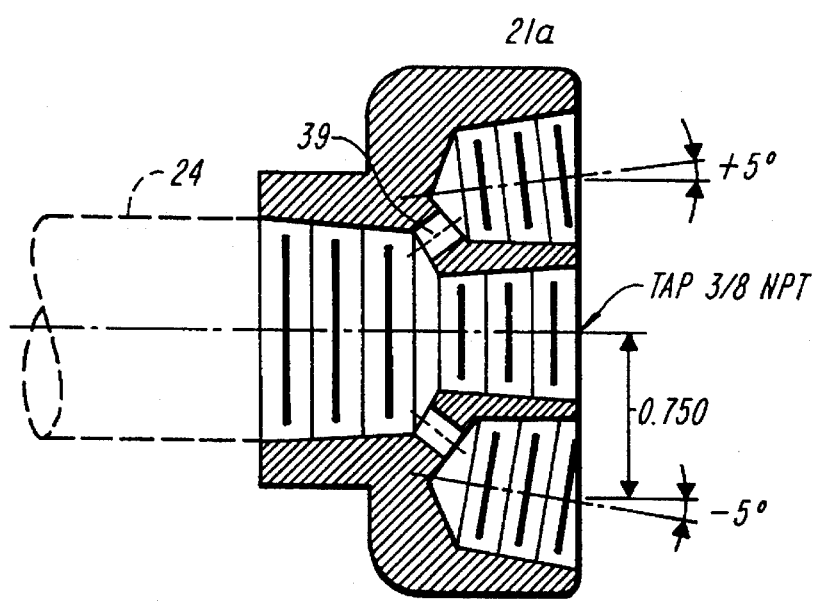
FIG. 4A is a sectional view of the transducer of FIG. 4.

As shown in sectional view, FIG. 4A, each of the transducer elements 31a through 31f has a pipe threaded ending adapted to screw into head 21a, and each threaded receiving recess is outwardly angled five degrees from the central axis. A passage 39 leads from each threaded recess to the center of the shaft 24. As noted above, synchronous activation of the transducer elements produces a multi-lobed beam, assuring that as temperature and flow conditions change a substantial portion of the beam energy always reaches the opposed receiving transducer.

Figure 5:
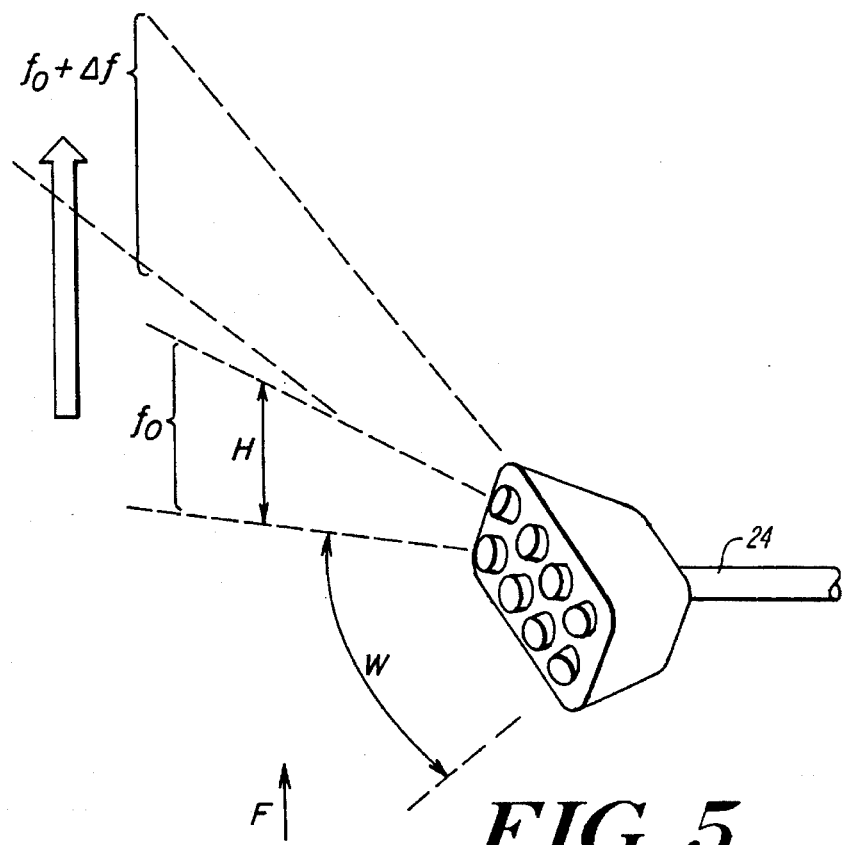
FIG. 5 shows a third transducer unit.

FIG. 5 shows yet another embodiment of the invention, wherein an array of transducers are arranged in a rectangular pattern, illustratively two elements high by four elements wide, the first and second horizontal rows of four elements being arranged in first and second planes spaced $\lambda/2$ apart. Preferably, the beam produced by the array is steered, as described above with reference to elements 60, 90 of FIG. 3, by varying the drive frequency to cause the beam to sweep in a direction parallel to the short side of the array. The use of four adjacent elements is intended to produce a controllably concentrated beam pattern in the horizontal plane, while the offset second row of four elements allows the resultant beam to be swept through many degrees for re-centering the beam vertically on an opposed receiving transducer. Beam sweeping is effected by simply changing the activation frequency until a strong received signal is detected. The four adjacent elements may each be aimed slightly off-axis, e.g., about two to five degrees on either side of the axis, so that their collectively large aperture does not result in too narrow a beam.

As before, both the receiving and transmitting transducers may, and advantageously do, take this form, with a pairwise differential amplification circuit attached to two out-of-phase elements during the receiving cycle as described in regard to FIG. 3, to eliminate noise. The common mode noise cancelled in this way includes not only noise originating in or borne by the stack walls, but also such fluid-originating "flow noise", as arises due to cavitation, vortex shedding or turbulence, that reaches each of the paired transducer elements simultaneously, as well as noise emanating from sources outside the receiving aperture of the transducer.

One preferred form of transducer element assembly includes piezoelectrically activated elements, having epoxy bonding agents and/or a Curie temperature of about 400 degrees Fahrenheit. Since this temperature is close to the ambient operating range in many stack gas sensing environments, and since, in addition, a stack gas may be highly corrosive, a system would benefit from a cooling mechanism or other protective feature.

Figure 6:
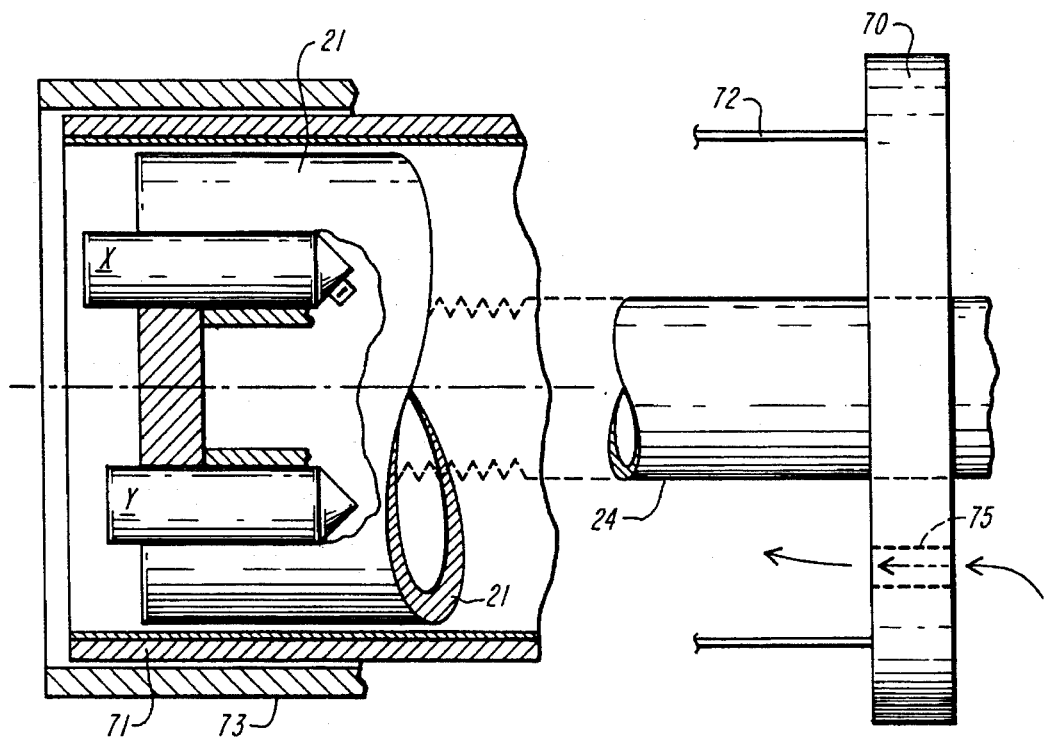
FIG. 6 illustrates a mounting assembly for the transducer units.

Such additional features are achieved for one embodiment of this invention as illustrated in FIG. 6, wherein a transducer assembly 21, 24 extends from its mounting flange 70 within tubular structure 72 protected within a surrounding shield layer 71 formed of a combination of a hard, wear-resistant material, e.g., steel, and a softer sound-absorbant material like Teflon. An end cap 73 surrounds the open end of the access conduit or transducer assembly so that vertically flowing stack gas does not directly contact the transducer assembly. This structure may also be readily adapted to provide passive cooling for the array in circumstances wherein the pressure of the stack gas is below atmospheric pressure. Such modification to provide cooling is achieved, for example, by providing vent passages 75 to the outside atmosphere opening into the flanged access assembly. The lower pressure prevailing in the stack draws air in through the access conduit, past head 21, bathing the transducer assembly in cool air and preventing transducer deterioration. No electrically-pumped purge system is necessary in this instance.

It will be appreciated that in describing the foregoing embodiments of the invention, detailed attention has been paid to the layout and activation of the transducer assemblies, while the description of complete flow measurement systems has been more briefly indicated since in many respects the implementation of systems follows known arrangements of transducers. It will be understood, however, that the systems for which these transducer assemblies were conceived include counterpropagation measurement systems, wherein two identical transducer assemblies are each alternatively used for transmitting and for receiving energy. Accordingly, when using the fixed spacing biphasic arrays of FIGS. 2 or 5, when it is desired to steer the beam to compensate for changed transducer alignment or unusual fluid conditions, it will generally be necessary to apply different corrections $\Delta f$ to the transmission frequency of the upstream and the downstream transducers. Accordingly, the invention contemplates systems of differently-facing transducer assemblies which are activated with different frequency pulse trains to achieve a desired propagation path. The invention further contemplates other specific numbers and arrangements of transducer elements within an assembly. For the corrosion resistant transducer elements shown in FIGS. 2 and 5, small finite arrays of $2n$ transducers are contemplated, while for the divergent assembly of FIG. 4 any small number, odd or even, from two to ten transducers are preferably symmetrically arranged on the head 21 or 21a.

The invention being thus disclosed and the implementation of several embodiments described, variations and modifications will occur to those skilled in the art, and all such variations are intended to be within the scope of the claims appended hereto.

What is claimed is:

1. A sensing system for detection of an ultrasonic interrogation signal transmitted through a gaseous fluid to determine a characteristic of the fluid, such sensing system comprising a receiving sensor including a body for holding a plurality n of ultrasonic transducer elements, said body being mounted in use to orient each of the transducer elements toward the fluid, said plurality n of ultrasonic transducer elements mounted in said body, wherein n>2, each respective element of the n ultrasonic transducer elements having a face for directly coupling energy between said respective element and fluid along an axis of signal propagation, said transducer elements mounted in the body operating at a frequency having a characteristic ultrasonic wavelength $\lambda$ in the fluid, and being arranged in pairs, each element of a pair having its face offset a distance $\lambda/2$ along it axis of propagation from the face of the other element of the pair.

2. A sensing system according to claim 1, further comprising differential combining means for differentially combining signals from both elements of a pair to null noise reaching both elements substantially simultaneously.

3. A sensing system according to claim 1, further comprising a transmitting transducer, said transmitting transducer being oriented in operation to direct sound energy through said fluid at said receiving sensor.

4. A sensing system according to claim 3, wherein said transmitting transducer is driven by an electrical signal to project energy through said fluid, said transmitting transducer including pairs of elements having energy coupling faces offset by $\lambda/2$, and further comprising means for driving one element of a transmitting pair with a signal inverted from a drive signal for the other element of the transmitting pair, thereby producing a substantially plane wavefront from plural elements acting in different planes.

5. A sensing system according to claim 3, wherein the transmitting transducer operates at a frequency of between 10 kHz and 100 kHz.

6. A sensing system according to claim 5, wherein the transmitting transducer operates at a frequency of about 50 kHz.

7. A sensing system according to claim 1, wherein the receiving sensor includes two to four pairs of transducer elements.

8. A sensing system according to claim 1, wherein the receiving sensor couples energy of the fluid through a surface area of less than about seventy-five square centimeters.

9. A sensing system according to claim 1, wherein each transducer element of said plurality of elements includes a diaphragm through which it couples energy into the fluid.

10. A sensing system according to claim 4, wherein said transmitting transducer is identical in construction to said receiving sensor.

11. A sensing system according to claim 1, wherein said body includes a head for holding the transducer elements, and an elongate body extending from the head for projecting the head into a stream of the fluid.

12. A sensing system according to claim 1, wherein the body is made of metal.

13. A sensing system according to claim 3, further comprising means for sweeping a drive frequency of said transmitting transducer to steer energy at said receiving sensor.

14. A sensing system according to claim 1, further comprising means for shrouding said receiving sensor from impact.

15. A sensing system according to claim 1, further comprising means for passively directing cooling air at the body.

16. A sensing system according to claim 1, wherein each pair constitutes a column of a rectangular array, the array having more columns than rows.

17. A sensing system according to claim 16, having two rows.

18. A sensing system according to claim 17, further comprising means for varying a transducer actuation frequency to steer an output or reception beam direction.

19. A sensing system according to claim 3, wherein ones of said elements have coupling faces directed between about two and five degrees from a common direction.

20. An ultrasonic transducer system for gas flow interrogation, such system comprising a body having a surface facing the gas and a plurality ultrasonic of transducing elements extending from the surface toward the gas, each element being oriented by said body to transduce ultrasonic energy directly in said gas along a different axis, offset slightly in direction from a common central axis of said transducing elements, and at least one pair of said elements including a first element and a second element having faces which are positioned offset from each other by a distance along said central axis equal to a half wavelength of said ultrasonic energy in the gas.

* * * * *